ature Patent [19]

United States Patent [19]  [11] 3,933,030
Forster et al.  [45] Jan. 20, 1976

[54] SYSTEM FOR CONTINUOUS MONITORING OF THE DENSITY OF CRYOGENIC LIQUIDS VIA DIELECTRIC CONSTANT MEASUREMENTS

[75] Inventors: Eric O. Forster, Scotch Plains; William R. L. Thomas, Holmdel, both of N.J.

[73] Assignee: Exxon Research and Engineering Company, Linden, N.J.

[22] Filed: Sept. 9, 1974

[21] Appl. No.: 504,143

[52] U.S. Cl. ................ 73/32 R; 62/49; 62/125; 62/129; 324/61 R
[51] Int. Cl.² ................ G01N 9/00; F17C 13/02
[58] Field of Search ............ 73/32 R, 53, 304 C; 324/61 R, 71 R; 317/246; 62/49, 125, 129; 340/200

[56] References Cited
UNITED STATES PATENTS

| | | | |
|---|---|---|---|
| 3,010,319 | 11/1961 | Sontheimer | 73/32 X |
| 3,222,918 | 12/1965 | Kuntz et al. | 73/53 |
| 3,276,214 | 10/1966 | Wilson et al. | 62/49 |
| 3,633,372 | 1/1972 | Kimmel | 62/49 |
| 3,638,442 | 2/1972 | Hedstrom | 62/49 |
| 3,665,209 | 5/1972 | Webb et al. | 324/61 R |
| 3,728,897 | 4/1973 | Wallman | 73/304 C |
| 3,813,924 | 6/1974 | Agar | 73/53 |

*Primary Examiner*—Richard C. Queisser
*Assistant Examiner*—Stephen A. Kreitman
*Attorney, Agent, or Firm*—Joseph J. Allocca

[57] ABSTRACT

A system has been invented for the continuous determination of density of cryogenic liquids such as LPG and LNG to within ± 0.1% or better using differential capacitance measurements. This system would allow the detection of incipient density inversions in storage tanks and the accurate determination of quantities transferred from ship to shore to customers.

11 Claims, No Drawings

SYSTEM FOR CONTINUOUS MONITORING OF THE DENSITY OF CRYOGENIC LIQUIDS VIA DIELECTRIC CONSTANT MEASUREMENTS

This invention relates to the utilization of capacitance probes for the continuous monitoring of the thermodynamic (density) conditions of cryogenic liquids such as LPG, LNG, ethane, propane or butane contained in a storage tank. In one aspect, the invention is a safety system capable of determining the existence of unstable conditions leading to the hazardous rollover phenomenon which is normally accompanied by the sudden evolution of large quantities of highly flammable and potentially explosive gases. In another aspect, the invention is a highly accurate method of determining actual density of the subject material and thereby facilitates accurate determination of quantities sold to customers insuring a higher degree of equity than is currently available.

Normally, it is a rather routine matter to determine the density of a liquid. It is considerably more difficult to carry out such a determination when dealing with liquefied gas, cryogenic liquids, such as mixtures of $C_1$ through $C_5$ hydrocarbons, in LNG or LPG, or mixtures of liquefied noble gases. These measurements are further complicated if frequent measurements are desired such as while transferring such liquids from ship to shore to customer so as to insure equity in billing. Also, these determinations are desirable on a continuous basis for safety reasons when dealing with large storage tanks. In these storage tanks it has been noted that density inversions can occur which, when left unchecked, can lead to sudden emission of large quantities of highly flammable gases and hence to explosions. This phenomenon, known as Rollover, typically occurs when the following sequence of events arise. A cryogenic tank containing a heel of some tens of thousands of bbls of LNG in a stable condition of low tank pressure and light composition is subsequently filled with a cargo of some hundreds of thousands of bbls of LNG from a tnaker, said LNG being of high tank pressure, higher temperature and heavy composition as a result of continuous boil-off of light components during shipping and heat absorption while waiting to offload. When this heavier, hotter, higher vapor pressure cargo from the tanker is transferred to the storage tank via bottom loading nozzles, the dense offloaded caargo stays on the bottom. The lighter, colder, lower vapor pressure initial tank heel is displaced upwards in the storage tank with only minimal mixing with the offloaded cargo. The static pressure of the initial tank heel suppresses vaporization of the higher vapor pressure cargo in the tank bottom.

During transfer, thorough mixing would result in the generation of many hundreds of thousands of pounds of vapor which would be vented to the atmosphere or recirculated through a cooling system. However, absent mixing, this potential vapor remains trapped in the contents of the tank and this situation presents an explosion hazard.

The ship's cargo was more dense than the tank heel even though it was warmer. This temperature difference between the layers causes a rapid transient transfer of heat from the bottom layer to the top layer. The ship's cargo cannot equilibrate to the tank pressure until its density is equal to or less than the density of the initial tank heel. The transfer of heat to the upper layer causes it to increase in temperature and density due to boil-off of lighter components and the consequent concentration of heavier components. The lower layer is simultaneously cooled by this heat transfer but at a rate offset by heat flow perhaps from the bottom and sides of the tank. This results in the top layer increasing in density faster than the lower layer and the two layers attaining equal density before the temperature can equilibrate. At this point, the now more dense upper layer collapses into the less dense lower layer and intense mixing occurs which causes tremendous volumes of vapor to be generated. To avoid this eventuality, it is necessary to know when an unstable density gradient exists in the tank.

Numerous techniques currently exist for determining the density of a liquid. The majority of these techniques are direct ones, that is, they measure the weight of a known volume of material. These measurements get more difficult if they have to be carried out on volatile liquids and they are extremely complex when operation at cryogenic temperatures is required. Hydrometers measure the liquid volume displaced by a known weight and the read-out scale is obtained by calibration with respect to reference systems at the temperature of common usage. This system suffers from the inherent disadvantage of requiring that a sample be taken for testing which exposes the sample to ambient air temperature and volatilization and thereby to inaccuracy. The Fixed Volume method attempts to balance the buoyance forces of the liquid acting on a body of known volume. Of particular interest are the levitation devices which use an external means to compensate the buoyancy forces acting on a float. Such a system requires elaborate experimental set ups such as electromagnets to achieve the desired precision. They further require that samples be taken and, therefore, are not suitable for continuous monitoring safety systems.

Differential pressure methods use two bubblers tubes which are inserted in the sample liquid so that the end of one tube is lower than that of the other. Hence, the pressure required to bubble air into the fluid is equal to the pressure of the fluid at the ends of the tubes, the pressure difference between the two tubes will be the same as the weight of a constant height column of the liquid of known volume. The differential pressure can be represented directly as density.

Under cryogenic conditions there occurs icing as well as volume changes in the tubes which can lead to erroneous density measurements and requires frequent recalibration of the units. Further, the physical movement necessitated by such bubblers (i.e. inserting the tubes and forcing air to bubble in the liquid) introduces inherent inaccuracy and finally the system cannot be directly mounted on or in the tank for use on a continuous basis.

Vibrating or resonating methods operate on the principle that the resonant frequency of an object depends on the total mass of the oscillating system. The fluid's density will therefore alter the frequency of oscillating of a cylinder when the latter is immersed in the liquid. This system has the drawback of requiring the presence of moving parts in the cryogenic liquid. Dip tube samples were also utilized which were inherently inaccurate due to mixing problems and volatilization of the sample. These samples were then analyzed by Gas chromatography to determine exact composition which introduced more error. Then the percent contribution of each component to density was determined and summed and a final density was arrived at. This procedure is time consuming and again suffers from the necessity of taking a sample and exposing it to ambient air temperatures and the additional step of G. C. Further, it has an accuracy of at best ± 0.5%. For the purpose of monitoring density inversion, it is necessary to know the density at various points in the tank to at least ± 0.2%, preferentially to ± 0.1% or better. Further, dip tube cannot be considered a continuous monitoring system which is desirable for rollover by triggering pumps and circulators.

Kuntz (U.S. Pat. No. 3,222,918) teaches the use of a capacitance cell to determine the density and basic sediment and water content of oil; it is an oil quality determinator. The process is specifically practiced by removing samples of oil from tank or pipeline and subjecting this test sample to controlled conditions of temperature, pressure and pretest preparation. The patent does not teach an in situ probe device for testing the absolute density of a material in a tank nor for the taking of a density profile of the contents of a tank to create a safety system.

Patterson (U.S. Pat. No. 3,698,513) utilizes a sonar type device which determines composition by measuring the velocity of sound passing through the material. The property measured is, therefore, different from the one measured by the instant invention as Patterson measures a chemical property by means of a physical (velocity of sound) method rather than a physical property by means of an electrical (capacitance dielectric constant) method. Further, Patterson's device is not a means of introducing safety into an operation whereas the instant invention is a system which senses density variations and remedies hazardous conditions.

Petrick (U.S. Pat. No. 3,474,337) discloses the determination of the properties of a liquid by passing "DC pulses" down a transmission line and measuring the time it takes for a return pulse to "bounce" off a discontinuance. For this system to work, it is necessary that recognizable interfaces exist between layers. This system could not measure density variations in a uniform homogeneous liquid wherein the density differences are not sufficient to form actual layers. By the time an appreciable layer interface has formed in a LPG LNG Tank which could be measured and determined by the Petrick system rollover conditions are present and possibly beyond the scope of preventive measures. Further, the physical implementation of this system is obviously different from the instant invention. The instant invention measures a physical constant, the dielectric constant and does so very accurately. The Petrick system depends on pulse echo return from a discontinuance and hinges upon measuring time differentials. Therefore, the system depends on data inputs which are subject to errors which, when present, are magnified when calculations are made. Finally, the fast rise time required to generate the D.C. Pulse makes it impossible to make the system "intrinsically safe" since low impedance circuits must be utilized along with high voltage in the vicinity of the probe itself which creates a spark hazard which is obviously unacceptable when dealing with liquefied natural and petroleum gases.

Nagel (U.S. Pat. No. 3,226,615) discloses the use of a capacitance probe to measure dielectric constant changes in the flow of a gas stream due to variations in dust content. The probe used is stationary with the material to be measured flowing past the probe. Therefore it is not determining a profile of the contents of a tank and as such would be of no use in a cryogenic system as a means of determining density variations in anticipation of rollover situations.

It has now been found, and forms the basis of the invention, that the density profile of cryogenic liquids, such as LNG, LPG, ethane, propane or butane at temperatures from $-40° \rightarrow -215°C$., can be continuously determined electrically by the use of differential capacitance measurements. The invention comprises the steps of continuously determining the dielectric constant of the cryogenic liquid, measuring the temperature of the cryogenic liquid, calculating the density of the cryogenic liquid to an accuracy of ±0.1% or better in a single operation by using the dielectric constant in the Clausius-Mosotti equation. For this purpose, numerous dielectric cells of known empty capacitance are used and are either suspended vertically at some predetermined interval in the tank thereby taking numerous simultaneous measurements of dielectric constant of the contents of the tank attached to a drum or winch is moved slowly (i.e. no more than 10 feet/min.) vertically through the cryogenic liquid thereby taking sequential readings of dielectric constant. In this way, a continuous reading of the dielectric constant of the contents of the tank is obtained and the density profile of the cryogenic liquid in the tank can be computed. An operator or computer continuously monitors the density thus obtained and triggers a pump or circulation system upon monitoring any density variations in the tank, thereby preventing rollover.

The individual density measurements making up the continuously monitored density profile are reproduceable to an accuracy of ±0.01% of the relative density of the cryogenic liquid in the tank.

The principle underlying this invention is the well known relationship between dielectric constant and density as defined by the Clausius-Mosotti equation:

$$\frac{\epsilon - 1}{\epsilon + 2} \cdot \frac{1}{C} = \rho$$

where C is the Clausius-Mosotti constant, $\epsilon$ = dielectric constant and $\rho$ = density. The value of C is given by the expression:

$$C = \frac{4 \pi N_A}{3} \cdot \frac{\epsilon \, m_i \alpha_i}{\epsilon \, m_i \, M_i}$$

$\alpha$ = molar polarizability
$m_i$ = mole fraction
$M_i$ = mole weight,
$N_A$ = Avogadro's number While it is known to use the dielectric constant measured by means of capacitors to calculate density, the novel concept of the present invention is to take continuous simultaneous or sequential readings of density in a cryogenic tank so as to monitor density changes and thereby obtain a density profile of the content of the tank creating a safety system to avoid the occurrence of rollover. In this utilization of the invention, the interest is not directed solely to the determination of density per se but to keep a constant alert monitor on density and density changes and thereby anticipate hazardous conditions sufficiently in advance to take preventive measures.

In the area of billing and inventory control, the instant constant monitor system will be a marked advance in the state of the art in cryogenic measurement and will enable marketers to determine the amount sold with remarkably improved accuracy independent of absolute knowledge of the exact composition of the LNG or LPG involved.

With the instant invention, we eliminate the necessity of taking samples and subjecting them to test. Here the dielectric constant is determined instantaneously by means of sensors in the tank, shielded by the very contents of the tank from error introduced by exposure of samples to ambient air temperatures and from the dielectric constant, density is calculated. The instant invention could not be practiced with as high a degree of accuracy by using a capacitor probe in a flow line since density changes would be introduced by the pumping action and also by heat take up in the pipes. Knowledge of exact composition of the material is unimportant since the cell reads the dielectric constant of the material present and the absolute density of the subject material is thereby determined.

Further, exact composition is not necessary since LNG is sold by density or by heat content/unit volume and to determine this, exact knowledge of composition is unnecessary. A buyer is not interested in knowing exact composition, but in getting fair volume charges and knowing what the BTU content/unit volume is. No prior method is known which will give this information with the accuracy and ease of the current invention.

The capacitors used in the process may be hung in multiples in the tank at predetermined intervals or mounted on a pole or rod at set intervals and then the entire pole or rod is introduced into the tank through existing flanges and access panels on the top of the tank without interrupting tank operation. Alternatively, when the tank is subjected to overhaul or is in the process of construction, the capacitors can be built right into the inside wall at the predetermined intervals. These multiple cells give continuous and simultaneous readings of the dielectric constant at many points in the tank from which density can be readily determined yielding a density profile which will warn of density inversions and rollover conditions.

EXAMPLE 1

Experiments were carried out in the 400,000 bbl LPG tank at the Everett Terminal of Exxon Company, U.S.A. Initially, three probes were installed in the tank at different levels to determine the existence of possible density gradient that could lead to rollover problems. The three commercially available stainless steel capacitance cells together with platinum resistance thermometers were introduced into the tank through an existing six-inch flange which was modified with a gate valve thereby not disrupting tank operation. Once installed the unit is sealed to prevent any escape of gas from the tank.

Preliminary calibration of the components used was performed in the laboratory and the dielectric constant of pure propane ($C_3$) and n- as well as isobutane ($C_4$), were determined between −45° and −55°C. A mixture containing 90 mole % $C_3$, 5 mole % n-butane and 5 mole % isobutane ($C_4$) was tested. The G.C. analysis of these samples, however, proved difficult. Whereas the error in reading capacitance was less than 0.05%, (the dielectric constant value was estimated to be good to ±0.05%), the analysis of the major gas components proved to be at best within ±3.0%. Calculation however predicted that the maximum error introduced by the use of an average typical LPG composition (95 mole % $C_3$ and 5 mole % $C_4$) rather than the actual composition would be ± 0.1%. This meant that one could predict the density of any mixture containing between 90 to 100 mole % $C_3$ and from 10 to 0 mole % $C_4$ from linear mixing laws to within ± 0.1%. That is, the constant relating the dielectric constant to the density changed only by 0.2% over this broad range of composition. See Table I.

TABLE I

Computation of Density and Dielectric Constant, $\epsilon$, at −44.5C for LPG Case For pure $C_3$ $\epsilon = 1.8066$ and for pure $C_4$ $\epsilon = 1.8964$ from laboratory measurements. Using $$\frac{\epsilon-1}{\epsilon+2} \cdot \frac{1}{C} = \delta$$

where $$C = \frac{4\pi}{3} N_A \frac{\alpha}{M}$$

for a pure material, we compute $\delta = 0.5810$ for $C_3$ and $\delta = 0.6450$ for $C_4$. To obtain $\epsilon$ and C for a mixture we use $\epsilon_x = m_1 \epsilon_1 + m_2 \epsilon_2$ where $m_1$ and $m_2$ are mole fractions of $C_3$, $C_4$ respectively. C is obtained similarly using $$C = \frac{4\pi}{3} N_A \cdot \frac{\epsilon\, m_i \alpha_i}{\epsilon\, m_i M_i}$$

where $\alpha_i$ and $M_i$ are the polarizability and mole weight of the $i$'th species.

Table I

| Composition Mol Percent | | | |
|---|---|---|---|
| $C_3$ | $C_4$ | $\epsilon$ | $\delta$ |
| 0 | 100 | 1.8964 | 0.6450 |
| 90 | 10 | 1.8156 | 0.5876 |
| 93 | 7 | 1.8129 | 0.5857 |
| 95 | 5 | 1.8111 | 0.5847 |
| 96 | 4 | 1.8102 | 0.5839 |
| 97 | 3 | 1.8093 | 0.5830 |
| 98 | 2 | 1.8084 | 0.5823 |
| 100 | 0 | 1.8066 | 0.5810 |

The three probes were hung in the tank at three levels, 5, 35 and 65 feet off the bottom of the tank. Tables II and III summarize the results of the test.

It was recognized that the density difference indicated by the middle probe could be the result of calibration error. Such error was plausible because of the difficulty encountered in the laboratory in producing constant temperature conditions at the low temperatures. The Everett tank on the other hand represented a much more stable temperature system.

Table II

| | Dielectric Constants ($\epsilon$) Read From Probes in LPG Tank (Liquid Level at 68 Ft.) | | | | | |
|---|---|---|---|---|---|---|
| | Bottom (~5 ft. from bottom) | | Middle (~35 ft. from bottom) | | Top (~65 ft. from bottom) | |
| | Temp., °C. | $\epsilon$ | Temp., °C. | $\epsilon$ | Temp., °C. | $\epsilon$ |
| 6/26 | −44.43 | 1.8082 | −44.52 | 1.8109 | −44.52 | 1.8091 |
| | | 1.8083 | | 1.8110 | | 1.8091 |
| | | 1.8083 | | 1.8110 | | 1.8091 |
| | | 1.8083 | | 1.8111 | | 1.8094 |
| | | 1.8084 | | 1.8111 | | 1.8096 |
| | | 1.8091 | | 1.8111 | | 1.8096 |
| | | 1.8092 | | 1.8112 | | 1.8097 |
| | | 1.8085 | | 1.8114 | | 1.8098 |
| | | 1.8089 | | 1.8112 | | 1.8099 |
| | | 1.8085±0.0002 | | 1.8111±0.0002 | | 1.8094±0 |
| 6/27 | −44.38 | 1.8080 | −44.47 | 1.8109 | −44.57 | 1.8092 |
| | | 1.8080 | | 1.8108 | | 1.8090 |
| | | 1.8084 | | 1.8110 | | 1.8089 |
| | | 1.8081 | | 1.8116 | | 1.8091 |
| | | 1.8080 | | 1.8106 | | 1.8099 |
| | | 1.8080 | | 1.8108 | | 1.8089 |
| | | 1.8079 | | 1.8109 | | 1.8089 |
| | | 1.8081±0.0002 | | 1.8109±0.0002 | | 1.8091±0 |

Table III

Temperature and Density Distrubtion in LPG Tank at Everett

| 6/26 | Bottom | Middle | Top | Average |
|---|---|---|---|---|
| T,C | −44.43 | −44.52 | −44.62 | −44.52 |
| $\rho$ | 0.5823 | 0.5847 | 0.5830 | 0.5833 |
| 6/27 | | | | |
| T,C | −44.38 | −44.48 | −44.57 | −44.47 |
| $\rho$ | 0.5821 | 0.5845 | 0.5829 | 0.5831 |

Average composition 96.5 mol % $C_3$ and 3.5 mol % $C_4$.

Analysis reported to Everett from GC analysis of sample removed 6/25: 3.4 % $C_2$, 94.4% $C_3$ and 3.2% $C_4$.

To alleviate and mitigate the problem, it was decided to run another set of tests in which one probe would be moved gradually vertically through the liquid to obtain a density profile which would not be influenced by any error in calibration. The probe was lifted by six foot increments and permitted to measure dielectric constant at each stop. Table IV summarizes the results of this test and shows that no significant density gradient exists as can be seen from the uniform dielectric constants which were measured.

Table IV

Profile of Dielectric Constants in LPG Tank Everett Temp. (−44.2±0.1) C Liquid Level at~62 ft. from bottom, 7/23−24/74

| | Dielectric Constant | | |
|---|---|---|---|
| Position | Probe 3 | Probe 2 | Probe 1 |
| A | 1.8098 | | |
| B | 1.8098 | | |
| C | 1.8098 | | |
| D | 1.8097 | | |
| E | 1.8097 | | |
| F | 1.8097 | 1.8097 | |
| G | 1.8097 | 1.8098 | |
| H | 1.8096 | 1.8097 | |
| I | 1.8096 | 1.8097 | |
| J | 1.8095 | 1.8096 | |
| K | 1.8096 | 1.8096 | 1.8096 |

Position A = ~5 ft. off the bottom. All others 6 feet apart except K which is at~61 feet off bottom, i.e., 2 ft. from J.

For $\epsilon$ = 1.8097.    $\delta$ = 0.5835.

What is claimed is:

1. A process for obtaining continuous and simultaneous multiple density measurements of cryogenic liquids at temperatures between −40° to −215°C. in storage tanks yielding an accurate density profile of the cryogenic liquid stored in the tanks to avoid rollover and obtain accurate billing data consisting of the steps of making numerous simultaneous measurements of the dielectric constant and temperature of the cryogenic liquid by means of numerous probes spaced vertically in the tank at some predetermined interval, determining the density using the dielectric constant in a single step independent of knowledge of the absolute material composition of the cryogenic liquid, continuously monitoring the density profile and triggering a pump or circulation system upon monitoring density stratification or inversion in the tank to avoid the occurrence of rollover.

2. A process for obtaining continuous and sequential density measurements of cryogenic liquids at temperatures between −40° to −215°C in storage tanks yielding an accurate continuous density profile of the contents of the tank to avoid rollover and obtain accurate billing data consisting of the steps of making numerous sequential measurements of the dielectric constant and temperature of the cryogenic liquid by means of a moving probe which probe moves vertically through the cryogenic liquid at no more than 10 feet per minute, calculating the density using the dielectric constant in a single step independent of knowledge of the absolute material composition of the cryogenic liquid, continuously monitoring the density profile and triggering a pump or circulation system upon monitoring density stratification or inversion in the tank to avoid the occurrence of rollover.

3. A process for obtaining continuous and simultaneous multiple density measurement of cryogenic liquids at temperatures between −40° to −215°C. in storage tanks yielding an accurate density profile of cryogenic liquids stored in tanks to avoid rollover and obtain accurate billing data consisting of the steps of making numerous simultaneous measurements of the dielectric constant and temperature of the cryogenic liquid by means of numerous probes spaced vertically in the tank at some predetermined interval, determining the actual density to an accuracy of at least ±0.1% using the dielectric constant in a single step independent of knowledge of the absolute material composition of the cryogenic liquid, continuously monitoring the density profile, wherein the individual density measurement making up the continuously monitored density profile are reproduceable to an accuracy of ±0.01% of the relative density of the cryogenic liquid in the tank, and triggering a pump or circulation system upon monitoring density stratification or inversion in the tank to avoid the occurrence of rollover.

4. A process for obtaining continuous and sequential density measurements of cryogenic liquids at temperatures between −40° to −215°C in storage tanks yielding an accurate continuous density profile of the contents of the tank to avoid rollover and obtain accurate billing data consisting of the steps of making numerous sequential measurements of the dielectric constant and temperature of the cryogenic liquid by means of a moving probe which probe moves vertically through the cryogenic liquid at no more than 10 feet per minute, calculating the actual density to an accuracy of at least ±0.1% using the dielectric constant in a single step independent of knowledge of the absolute material composition of the cryogenic liquid, continuously monitoring the density profile wherein the individual density measurements making up the continuously monitored density profile are reproducible to an accuracy of ±0.01% of the relative density of the cryogenic liquid in the tank and triggering a pump or circulation system upon monitoring density stratification or inversion in the tank to avoid the occurrence of rollover.

5. A process according to claim 1 wherein the cryogenic liquid is LNG.

6. A process according to claim 1 wherein the cryogenic liquid is LPG.

7. A process according to claim 1 wherein the cryogenic liquid is ethane.

8. A process according to claim 1 wherein the cryogenic liquid is propane.

9. A process according to claim 1 wherein the cryogenic liquid is butane.

10. A process for obtaining continuous and simultaneous multiple dielectric constant measurement of cryogenic liquids at temperatures between −40° to −215°C. in a tank which comprises making numerous simultaneous measurements of the dielectric constant of the cryogenic liquid by means of numerous probes spaced vertically in the tank at some predetermined interval which measurements are accurate to within 0.05% of actual dielectric constant and are reproduceable to within ±0.0002.

11. A process for obtaining continuous and sequential multiple dielectric constant measurements of cryogenic liquids at temperatures between −40° to −215°C in a tank which comprises making numerous sequential measurements of the dielectric constant of the cryogenic liquid by means of a moving probe which probe moves vertically through the cryogenic liquid at no more than 10 feet per minute, which measurements are accurate to within 0.05% of actual dielectric constant and are reproducible to within ± 0.0002.

* * * * *